United States Patent
Gennadios (12)

(10) Patent No.: US 6,193,999 B1
(45) Date of Patent: Feb. 27, 2001

(54) GUM ACACIA SUBSTITUTED SOFT GELATIN CAPSULES

(75) Inventor: Aristippos Gennadios, High Point, NC (US)

(73) Assignee: Banner Pharmacaps, Inc., High Point, NC (US)

( * ) Notice: Subject to any disclaimer, the term of this patent is extended or adjusted under 35 U.S.C. 154(b) by 0 days.

(21) Appl. No.: 09/259,708

(22) Filed: Mar. 1, 1999

(51) Int. Cl.$^7$ .............................. A61K 9/64; A61K 9/14; A61K 9/48; A61K 9/66; A61K 47/00
(52) U.S. Cl. .................... 424/456; 424/489; 424/451; 424/454; 424/452; 424/455; 424/439
(58) Field of Search .................................. 424/456, 489, 424/451, 454, 452, 455, 401, 439

(56) References Cited

U.S. PATENT DOCUMENTS

| | | | |
|---|---|---|---|
| 3,959,540 | 5/1976 | Leiberich et al. | 428/35 |
| 4,055,554 | 10/1977 | Helmstetter | 260/117 |
| 4,350,679 | 9/1982 | Mizuno et al. | 424/38 |
| 4,804,542 | 2/1989 | Fischer et al. | 424/456 |
| 4,816,259 | 3/1989 | Matthews et al. | 424/463 |
| 5,554,385 | 9/1996 | Stroud | 424/456 |
| 5,614,217 | * 3/1997 | Chiprich | 424/451 |

OTHER PUBLICATIONS

"EU Proposes New Health Rules For Bovine–Sourced Materials", *Chemical Market Report*, 1 page, (Mar. 16, 1998).

Felton, L.A., et al., "Physical–mechanical properties of film–coated soft gelatin capsules", *International Journal of Pharmaceutics*, vol. 127, pp. 203–211, (1996).

Islam, A.M., et al., "A review of recent developments on the regulatory, structural and functional aspects of gum arabic", *Food Hydrocolloids*, vol. 11, No. 4, pp. 493–505, (1997).

Jizomoto, H., et al., "Gelatin–Acaia Microcapsules for Trapping Micro Oil Droplets Containing Lipophilic Drugs and Ready Disintegration in the Gastrointestinal Tract", *Phamaceutical Research*, vol. 10, No. 8, pp. 1115–1122, (1993).

Menzies, A.R., et al.,"A comparison of the physicochemical and immunological properties of the plant gum exudates of Acacia senegal (gum arabic) and Acacia seyal (gum tahla)", *Food Additives and Contaminants*, vol. 13, No. 8, pp. 991–999, (1996).

Pang, D.C., "Transmissible Spongiform Encephalopathies", *AAPS Newsletter*, pp. 9–12, (Apr. 1998).

Tirkkonen, S., et al., "Microencapsulation of indomethacin by gelatin–acacia complex coacervation in the presence of sufacatants", *J. Microencapulation*, vol. 11, No. 6, pp. 616–626, (1994).

Wilkinson, P.K., et al., "Softgels: Manufacturing Considerations", *Specialized Drug Delivery Systems*, pp. 409–449, (1990).

* cited by examiner

*Primary Examiner*—Thurman K. Page
*Assistant Examiner*—Blessing Fubara
(74) *Attorney, Agent, or Firm*—Rhodes & Mason, PLLC

(57) ABSTRACT

A soft-gelatin, extended gelatin composition has been found, which composition comprises a non-brittle shell forming material. The wet composition comprises:

a) 30–60% by weight of a film-forming material b) 5–35% by weight of a water-dispersible or water-soluble plasticizer c) 25–65% by weight purified water wherein the film-forming material comprises gelatin and gum acacia, with gum acacia accounting for 0.5–50% by weight of the total amount of the film-forming material, a dried film having 3–12% by weight of water formed from said composition having no reduced elasticity as compared to a film having the same proportions of the same water-dispersible or water-soluble plasticizer to the total weight of only gelatin film-forming material.

16 Claims, No Drawings

GUM ACACIA SUBSTITUTED SOFT GELATIN CAPSULES

FIELD OF THE INVENTION

The present invention relates to the field of soft gelatin capsules for oral delivery of pharmaceutical substances, nutritional supplements and the like. More particularly, it relates to soft gelatin capsule shell compositions that include gum acacia (gum arabic) as a partial substitute for gelatin. Such soft gelatin capsules may be manufactured in a conventional rotary die encapsulation machine.

BACKGROUND OF THE INVENTION

Gelatin is an animal-derived protein that finds a wide array of food, pharmaceutical, photographic, and technical applications. It has been used to manufacture various types of capsules for more than a hundred years, and those capsules have been utilized in a wide variety of industrial and commercial applications. Softgels (soft gelatin capsules) are a common dosage form for the administration of liquid, semi-solid and solid fills, and soft gelatin capsules embody a distinct classification of properties within the gelatin art. The typical softgel manufacturing process uses the rotary die encapsulation system, and such a general manufacturing process is described by Wilkinson, P. K. and Hom, F. S., 1990, "Softgels: manufacturing considerations." In: *Specialized Drug Delivery Systems*, P. Tyle (Ed.), pp. 409–449, Marcel Dekker, Inc., New York.

The primary components of the conventional capsule shell are gelatin, plasticizers and water. Several other minor shell additives may be present, such as coloring, opacifying, flavoring and antimicrobial agents. Extenders have been used in gelatin shell compositions to reduce the cost of materials within the shell and adjust the physical or chemical properties of the shell.

Gelatin is manufactured by controlled hydrolysis of collagen, which is present in the bones, skins, and white connective tissues of animals. Gelatin obtained from acid hydrolysis of collagen is known as Type A gelatin, whereas gelatin obtained from alkali hydrolysis of collagen is known as Type B gelatin. Commercially, the primary raw materials for gelatin manufacturing are pigskins, and bones and skins from bovine animals. The softgel industry mainly uses gelatin derived from bovine bones.

In recent years, a bovine spongiform encephalopathy (BSE), or "mad cow disease" outbreak in Europe (particularly in the United Kingdom) has affected the meat, rendering and gelatin manufacturing industries using bovine animals. BSE-infected cattle have been implicated, although not conclusively, in transmission of the neurodegenerative variant Creutzfeldt-Jacob disease (CJD) to humans. The suspicion centers on 21 variant CJD cases in the United Kingdom and one variant CJD case in France (Pang, D. C., 1998, "Transmissible spongiform encephalopathies." *AAPS Newsletter*, April 1998).

In response to the situation, certain bovine bones (e.g., skull and spinal column) are now classified as specified risk materials and are excluded from the raw material supply for gelatin (Anonymous, 1998, "EU proposes new health rules for bovine-sourced materials." *Chemical Market Reporter*, Mar. 16, 1998).

Also, the sun-dried bones of cattle dying from natural causes in India and Pakistan have lost some level of commercial acceptance due to lack of traceability. As a result, bone supplies for gelatin production have tightened up and prices have increased. Additionally, the potential for continued downturns in the consumption of beef or the reduction in beef production because of reduced profitability would portend for additional upward pressure on the price of bovine gelatin. There is also the probability of additional uses for gelatin which could further support higher prices. Overall, gelatin is a biopolymer in high demand and its market is expected to keep growing in the near future. Therefore, there is an apparent need for identifying inexpensive gelatin extenders that can partially replace gelatin in some of its commercial uses, such as in shell formulations of capsules. In addition to the obvious economical benefits, use of such gelatin extenders in capsules may also be accompanied by functional improvements.

U.S. Pat. No. 3,959,540 discloses an outer coating made of an acrylic polymer that renders softgels resistant to gastric juices and suitable for enteric release. The gelatin capsules comprise three layers: an inner gelatin shell, an intermediate layer comprising a cationic polymerizate of di-lower alkylamino lower alkylmethacrylate, and outer gastric juice resistant coating of an anionic polymerizate of methacrylic acid and acrylic acid esters.

Coating of softgel capsules with an acrylic film that possesses enteric release properties also is discussed by Felton, L. A., Shah, N. H., Zhang, G., Infeld, M. H., Malick, A. W. and McGinity, J. W. 1996. "Physical-mechanical properties of film-coated soft gelatin capsules." *International Journal of Pharmaceutics*, 127:203–211. The article describes that storage at low relative humidity causes an increase in the Young's Modulus for the capsules over time.

U.S. Pat. No. 4,816,259 discloses the application of a hydroxypropyl methylcellulose subcoating to the outer surface of a softgel. This subcoating improves the mechanical strength of the capsule and the capsule surface adheres better to known enteric coating compositions.

U.S. Pat. No. 4,350,679 discloses the application of a carnauba wax coating on a softgel. The functionality of the wax coating is to improve shell strength and moisture resistance.

All of the aforementioned systems involve coating finished (dried softgels in a "post-processing" step). It is preferable that polymeric additives of natural or synthetic origin that impart certain functionalities or are inexpensive gelatin extenders are incorporated into shell formulations during the gel mass preparation stage and prior to capsule formation, as increasing the number of manufacturing steps increases the time needed for manufacture and increases the cost of manufacture.

U.S. Pat. No. 4,055,554 discloses the use of chemically modified dialdehyde polysaccharides as gel strength enhancers for gelatin compositions. Such compositions may be used for manufacturing capsules.

U.S. Pat. No. 4,804,542 discloses a softgel wherein the capsule shell contains (at least 1% by weight) an additive capable of absorbing water in an amount of at least 10% by weight of its own weight. Such additives include starches, starch derivatives, celluloses, cellulose derivatives, and milk powder. Some non-hygroscopic materials such as mono-, di-, and oligosacchrides, lactose, magnesium trisilicate, and colloidal silica also are described as useful.

U.S. Pat. No. 5,554,385 discloses a softgel wherein the dry capsule shell is comprised of 3–60% starch having a high amylose content. This invention involves preparation of gel mass by combining gelatin, high amylose starch, plasticizers, water, and other minor additives. The gel mass is then processed with the rotary die encapsulation machine to manufacture softgels. The capsules of this invention have textured frosted or satin finish.

U.S. Pat. No. 5,614,217 discloses a softgel that has increased brittleness and can be broken with manual pressure. The shell formulation of such a capsule contains a non-hygroscopic plasticizer and an elasticity reducing extender. The extender is selected from a number of natural and synthetic polymers. The capsule of this invention cannot be plasticized with a conventional hygroscopic polyol such as glycerin or sorbitol. Instead, a non-hygroscopic plasticizer is used such as maltitol, maltitol syrup, partially dehydrated hydrogenated glucose syrup, and hydrogenated starch hydrolysate. Although brittle soft gelatin capsules may be desirable for some particular uses, it is desirable for many uses to be able to change from one composition of soft gelatin capsules having one feel (flexibility, texture, brittleness, etc.) to another soft gelatin capsule having a different composition but the same feel. This is particularly important in the commercial pharmaceutical industry where a change in the physical properties of a commercial item can lead to adverse consumer response.

Gum acacia or gum arabic or acacia (alternative names for essentially the same material which are used in the art) is a plant exudate collected from the trees of Acacia species. Chemically, it is an arabinogalactan-protein complex composed by weight of 17–34% arabinose, 32–50% galactose, 11–16% rhamnose, 13–19% glucuronic acid and 1.8–2.5% protein (Menzies, A. R., Osman, M. E., Malik, A. A. and Baldwin, T. C. 1996). A comparison of the physicochemical and immunological properties of the plant gum exudates of *Acacia senegal* (gum arabic) and *Acacia seyal* (gum talha) is provided in *Food Additives and Contaminants,* 13:991–999.

The chemical structure and functional properties of gum acacia are discussed in detail by Islam et al. (Islam, A. M., Phillips, G. O., Sljivo, A., Snowden, M. J. and Williams, P. A. 1997, "A review of recent developments on the regulatory, structural and functional aspects of gum arabic." *Food Hydrocolloids,* 11:493–505).

Commercially available gum acacia is a bland, tasteless, odorless, white to yellowish-white powder. Edible uses of gum acacia include emulsification and foam stabilization in beverages, emulsification in flavor emulsions and prevention of sugar crystallization in confectionery products. Also, gum acacia has been used in combination with gelatin, in particular Type A gelatin, for the preparation of microcapsules capable of entrapping micro oil droplets containing lipophilic drugs. For example, such microcapsules, which are formed with a coacervation method, are described by Jizomoto et al. (Jizomoto, H., Kanaoka, E., Sugita, K. and Hirano, K. 1993. "Gelatin-acacia microcapsules for trapping micro oil droplets containing lipophilic drugs and ready disintegration in the gastrointestinal tract." *Pharmaceutical Research,* 10:1115–1122) and by Tirkkonen et al. (Tirkkonen, S., Turakka, L. and Paronen, P. 1994. "Microencapsulation of indomethacin by gelatin-acacia complex coacervation in the presence of surfactants." *Journal of Microencapsulation,* 11:615–626).

BRIEF DESCRIPTION OF THE INVENTION

A soft-gelatin, extended gelatin composition for use in the manufacture of softgel capsules has been found, which composition comprises a non-brittle shell forming material. The wet composition comprises:
a) 30–60% by weight of a film-forming material
b) 5–35% by weight of a water-dispersible or water-soluble plasticizer
c) 25–65% by weight purified water
wherein the film-forming material comprises gelatin and gum acacia, with gum acacia accounting for 0.5–50% by weight of the total amount of the film-forming material, a dried film having 3–12% (e.g., 10–11% for testing purposes) by weight of water formed from said composition having no reduced elasticity as compared to a film having the same proportions of the same water-dispersible or water-soluble plasticizer to the total weight of only gelatin film-forming material. A soft gelatin capsule may be provided comprising a fill and a shell, wherein the shell comprises the dried material formed from that composition.

A process of manufacturing a filled soft gelatin capsule comprising a fill and a shell is also disclosed wherein a fill is provided to an encapsulation area where a sheet of soft gelatin material comprising 30–70% by weight of film-forming material and 58–27% by weight of water-dispersible or water-soluble plasticizer, and the sheet of soft gelatin material encapsulates the fill by the rotary die encapsulation process to form a filled soft gelatin capsule, wherein the shell comprises a dried film having less than about 20% by weight of water (e.g., 3–12%, 5–12%, or 8–12%) is formed from the composition, the shell having no reduced elasticity as compared to a shell having the same proportions of the same water-dispersible or water-soluble plasticizer to the total weight of only gelatin film-forming material.

DETAILED DESCRIPTION OF THE INVENTION

It has now been discovered that gum acacia can replace gelatin, in replacement amounts of from about 5 to 35% by total weight of gelatin in capsule-forming compositions, in thermally sealed, orally administered capsules manufactured with the conventional rotary die encapsulation machine, without increasing the brittleness of the shell. This is surprising, as it was taught in the art (U.S. Pat. No. 5,614,217, the Chiprich Patent) that gum arabic is an elasticity reducing agent for gelatin. It is postulated that, as evidenced by the limited number of actual elasticity reducing agents used in the examples, it was assumed that all classes of generally equivalent materials were expected to behave the same. The fact that the present invention has found that gum acacia does not reduce elasticity to any significant or measurable degree is therefore a surprising result with implications of broader utility for gum acacia than merely as one of a number of elasticity reducing agents as listed in U.S. Pat. No. 5,614,217. Besides economic benefits (gum acacia is currently cheaper than pharmaceutical grade gelatin by about 50%), extending gelatin with gum acacia in softgels results in the following possible functional advantages:

1) Shorter drying periods for formed capsules can be employed because gum acacia is a film-former but, in contrast to gelatin, is not a gel-former. Non-gelling biopolymers (e.g., gum acacia) do not entrap and hold water as strongly as gelling biopolymers (e.g., gelatin). Shortening of the drying process allows for highest throughput in the system.

2) Shorter aging times of gel masses can be practiced, thus again allowing for shortening production cycles and increasing throughput. In softgel manufacturing, a gel mass is prepared by melting under vacuum in a reactor the shell components (i.e., gelatin, plasticizer, water, and minor additives). The molten mass is dropped into receivers and is aged (conditioned) on heat for several hours to allow for suitable thermal breakdown prior to encapsulation. This breakdown improves the processing characteristics of the gel mass on the encapsulation machine such as its viscosity. This gel mass breakdown is accelerated and, therefore, required aging times are shortened, by including gum acacia as gelatin extender.

3) Shorter opening and disintegration times for finished capsules, which is attributed to the highly cold-water soluble nature of the gum acacia.

4) Color compatibility with conventional gel masses. Certain materials have a notable effect on gel mass color when used as gelatin extenders. For example, non-gelatin proteins (e.g., soy protein and wheat gluten) or milk powder have an opacifying ("milky") effect on gelatin compositions. Also, starch derivatives such as maltodextrins interact with gelatin through Maillard browning reaction yielding an intense brown coloration. Therefore, use of the aforementioned materials as gelatin extenders in colored capsules requires extensive color reformulation. In addition, such extenders negatively affect the appearance of clear (non-colored) capsules, which are popular with certain nutritional oil-based fills (e.g., vitamin E and lecithin). In contrast, gum acacia is highly soluble in cold water yielding clear solutions and, thus its use as a gelatin extender in capsules does not raise any color-related concerns.

5) Replacement of existing gelatin shell compositions in commercial products without noticeable consumer response from changes in the physical properties of the shell as compared to previous commercial products.

Typically, gel masses prepared for subsequent softgel formation may comprise 30–60% by weight of gelatin, 5–35% by weight of plasticizer, and the remainder comprising purified water, exclusive from consideration of other optional minor additives such as colorants, opacifiers, flavors, sweeteners, preservatives and medicaments. The gel masses are processed on an encapsulation machine, such as the rotary die encapsulation machine, where softgels are formed, filled, and heat-sealed in one continuous operation. Subsequently, the capsules are dried to approximate shell moisture content of 5–10% by weight.

According to the present invention, the gelatin in the capsule shell compositions described above is partially replaced by gum acacia. The amount of gelatin replaced by gum acacia may be from about 5% to 50% by weight of gelatin, and more preferably from 10 to 25% by weight of gelatin. Of course, gum acacia may be used to replace less than 5% by weight of the gelatin, however, at such low levels the advantages associated with use of gum acacia are minimal. Preferably, the gelatin used in the present invention is Type B gelatin, such as the gelatin derived from alkali-treated bovine bones and hides. However, mixtures of Type B gelatin and Type A gelatin (such as the gelatin derived from acid-treated pigskins) can be used, with Type A gelatin accounting for anywhere from 0 to 100% by weight of the total amount of gelatin or not more than 50% by weight of the total amount of gelatin.

Traditionally, hygroscopic plasticizers such as glycerin, sorbitol and alkylene glycols (e.g., propylene glycol and low molecular weight polyethylene glycols) have been used as shell plasticizers for softgels. Nowadays, plasticization of capsule shells with non-hygroscopic plasticizers (e.g., maltitol, lactitol, xylitol, hydrogenated starch hydrolysate and partially dehydrated hydrogenated glucose syrups) is also common. There are no restrictions in terms of plasticizer selection for the gelatin-extended capsules of the present invention. Any hygroscopic or non-hygroscopic plasticizer used with conventional softgels and mixtures of two or more of such plasticizers may be used. The rotary die encapsulation machine is particularly suitable for manufacturing capsules according to the present invention although other encapsulating devices may be used.

The feature of non-elasticity reduction in the practice of the present invention may be measured by the same procedures detailed in Felton, L. A., Shah, N. H., Zhang, G., Infeld, M. H., Malick, A. W. and McGinity, J. W. 1996. "Physical-mechanical properties of film-coated soft gelatin capsules." *International Journal of Pharmaceutics,* 127:203–211. A first gelatin-only composition comprising 45% by weight gelatin (film-forming material), 7% by weight glycerin, 17% by weight sorbitol solution, 6% by weight maltitol syrup and 25% by weight of purified water is used to manufacture soft gelatin capsules by a conventional rotary die process, and its elasticity measured. A second partial gelatin composition comprising 45% by weight film-forming material (comprising 80% gelatin and 20% gum acacia), 7% by weight glycerin, 17% by weight sorbitol solution, 6% by weight maltitol syrup and 25% by weight of purified water is used to manufacture soft gelatin capsules by a conventional rotary die process, and its elasticity measured. Identical fills are used in the two soft gelatin manufacturing processes. The elasticity of the soft gelatin capsules made by the rotary die process under the same conditions are compared, and if the elasticity from the second composition has not decreased, it is not an elasticity reducing agent. Elasticity may be measured in swatches of film more easily by any standard procedures and apparatus commonly used within the field of commercial or industrial testing for elasticity, including any available ASTM protocols. In later examples, elasticity was measured with a texture analyzer in which the percentage elongation at break was measured for swatches.

EXAMPLES

To further illustrate the practice of the present invention, the following examples of gum acacia substituted gelatin capsules are provided.

Example 1

A control (without gelatin substitution) gel mass was prepared in a per se known manner combining 41.7 kg of gelatin, 23.2 kg of glycerin and 35.1 kg of purified water. Also, a gelatin extended mass was prepared in the same manner by replacing 15% by weight of the gelatin with gum acacia (i.e., the mass comprising 35.4 kg of gelatin, 6.3 kg of gum acacia, 23.2 kg of glycerin and 35.1 kg of purified water). The two masses were separately processed on a rotary die encapsulation machine and oval-shaped sealed capsules filled with a mixture comprising 6% by weight soybean oil and 94% by weight vitamin E (DL-alpha tocopheryl acetate 1,000 IU) were prepared.

Finished (dried) capsules manufactured from control and gelatin-extended compositions were packaged into 50-count bottles made of high density polyethylene and stored at controlled conditions of 25° C. and 60% relative humidity. At storage time intervals of 0, 3 and 9 months, six control and six gelatin-extended capsules were tested for disintegration and opening times using acetate buffer (pH 4.50±0.05 maintained at 37±2° C.) as the immersion fluid. Testing was performed with Apparatus A described in the United States Pharmacopoeia. As shown in Table 1, both the control and the gelatin-extended capsules disintegrated within 8 minutes (which is well below the recommended maximum test limit of 45 minutes). Compared to control capsules, gelatin-extended capsules opened and disintegrated as fast or even faster (at least at 0 and 3 months). Also, no leakage of the fill was detected at any of the testing intervals, thus indicating that good seams were obtained for both the control and the gelatin-extended capsules. Finally, after 3 months storage at the above-mentioned environmental conditions, capsule fills were assayed for vitamin E, and the same potency values (390 IU) were determined for both control and gelatin-extended capsules. This indicated that the partial replacement of gelatin with gum acacia in the capsule shell presents no adverse effect for encapsulated actives.

TABLE 1

Disintegration and opening characteristics of gelatin and gelatin-extended softgels filled with soybean oil and vitamin E.

| Interval | Disintegration time (minutes) | | Opening time (minutes) | |
|---|---|---|---|---|
| (months) | Control | Gelatin-extended | Control | Gelatin-extended |
| 0 | 5:36–5:36 | 3:23–5:00 | 0:30–0:30 | 0:19–0:19 |
| 3 | 4:22–5:02 | 3:24–4:32 | 0:27–0:44 | 0:18–0:24 |
| 9 | 6:03–7:07 | 6:31–7:26 | 0:19–0:40 | 0:22–0:52 |

Example 2

A control gel mass was prepared by mixing 43.8 kg of gelatin, 24.5 kg of glycerin and 31.7 kg of purified water. Also, a gelatin-extended mass was prepared in the same manner by replacing 20% by weight of the gelatin with gum acacia (i.e., the mass comprising 35.04 kg of gelatin, 8.76 kg of gum acacia, 24.50 kg of glycerin and 31.70 kg of purified water). Oblong-shaped capsules were prepared from the two masses in a rotary die encapsulation machine. Each capsule was filled with about 1,470 milligrams of a multivitamin and mineral paste (comprised of vitamin A palmitate, vitamin C, vitamin D, vitamin E, vitamin B1, vitamin B2, vitamin B6, niacinamide, lecithin, wax, soybean oil, calcium pantothenate, cobalamin, dicalcium phosphate, ferrous sulfate, magnesium sulfate, potassium sulfate, zinc sulfate, and manganese sulfate).

Similar to Example 1, capsules were evaluated for disintegration and opening times after 0, 3, and 6 months of storage (25° C. and 60% relative humidity). As shown in Table 2, both control and extended capsules disintegrated within 13 minutes (which is well below the disintegration time of 45 minutes recommended for softgels filled with dietary supplements). Compared to control capsules, gelatin-extended capsules opened and disintegrated as fast or even faster (at least at 0 and 3 months). Also, no leakage of the fill was detected at any of the testing intervals, thus indicating that good seams were obtained for both the control and the gelatin-extended capsules.

TABLE 2

Disintegration and opening characteristics of gelating and gelatin-extended softgels filled with multivitamin and mineral paste.

| Interval | Disintegration (minutes) | | Opening time (minutes) | |
|---|---|---|---|---|
| (months) | Control | Gelatin-extended | Control | Gelatin-extended |
| 0 | 8:20–9:04 | 6:49–7:47 | 0:49–1:02 | 0:58–1:23 |
| 3 | 9:02–10:27 | 7:17–10:08 | 1:05–2:04 | 1:04–1:51 |
| 6 | 10:22–11:20 | 10:27–12:10 | 1:18–3:38 | 1:07–2:37 |

Example 3

A gelatin-extended gel mass was prepared by mixing 37.6 kg of gelatin, 9.4 kg of gum acacia, 15.0 kg of glycerin and 38.0 kg of purified water. Oval-shaped capsules were prepared from the two masses in a rotary die encapsulation machine using as fill a mixture comprising 94% by weight vitamin E (DL-alpha tocopheryl acetate 1,000 IU) and 6% by weight soybean oil. The formed capsules were dried to a shell moisture content of 8.3% by weight. The finished capsules were bottled on 50-count high density polyethylene bottles and stored at controlled conditions of 40° C. and 75% relative humidity. After three months storage, the capsules did not leak and they disintegrated within 20 minutes (which is well below the disintegration time of 45 minutes recommended for softgels filled with dietary supplements (which is well below the disintegration time of 45 minutes recommended for softgels filled with dietary supplements).

Example 4

A control gel mass was prepared by mixing 44.2 kg of gelatin, 7.0 kg of glycerin, 17.6 kg of sorbitol solution, 6.0 kg of maltitol syrup and 25.2 kg of purified water. Also, a gelatin-extended mass was prepared in the same manner by replacing 20% by weight of the gelatin with gum acacia (i.e., the mass comprising 35.36 kg of gelatin, 8.84 kg of gum acacia, 7.00 kg of glycerin, 17.60 kg of sorbitol solution, 6.00 kg of maltitol syrup and 25.20 kg of purified water). The masses were placed in stainless steel receivers and aged (conditioned) at 60° C. for about 48 hours to allow for suitable breakdown (reduction in dynamic viscosity) prior to encapsulation. At the end of the aging period, the dynamic viscosity of both masses was measured with a Brookfield viscometer. The control mass had a dynamic viscosity of 17,910 cP while the gelatin-extended mass had a dynamic viscosity of 8,580 CP. This demonstrates that gel compositions containing gum acacia as partial gelatin substitute break down on heat faster than conventional gelatin compositions. This offers the obvious advantage of shortening the required gel aging period prior to processing the gel on the encapsulation machine. Both gel mass compositions were unobjectionably processed in a rotary die encapsulation machine and oval-shaped capsules were manufactured. Each capsule was filled with about 435 milligrams of a mixture comprised of chondroitin sulfate, lecithin, wax and soybean oil. The gelatin-extended capsules were similar to control capsules in terms of physical characteristics.

Example 5

Even more surprising than the fact that the gum acacia did not reduce the elasticity of the gelatin extended compositions was the fact that an opposite effect was actually noted. As shown in the following Table 3, when a gum acacia-extended gelatin composition was compared to an otherwise identical gelatin composition (with the respective amount of film forming materials remaining constant; that is the total weight of the gelatin-only in one shell was equal to the total weight of gelatin and gum acacia in the other shell and all other proportions were the same). The gelatin compositions were tested as swatches of film, and the elongation to break was measured for the cast swatches. The comparative results actually showed increased elasticity in the gelatin-gum acacia compositions.

The compositions tested were comprised as follows:

Composition 3A gel mass comprises as percentages by weight, 41.7% gelatin, 23.2% glycerin, and 35.1% purified water. This is essentially the same composition described in Example 1, with the gelatin and gum acacia percentages adjusted accordingly for 10, 15 and 20% substitution (of the gelatin by gum acacia) of the gelatin.

| Component | 10% Substitution | 15% Substitution | 20% Substitution |
|---|---|---|---|
| Gelatin | 37.5% | 35.4% | 33.4% |
| Gum Acacia | 4.4% | 6.6% | 8.3% |
| Glycerin | 23.2% | 23.2% | 23.2% |
| Purified Water | 35.1% | 35.1% | 35.1% |

Composition 3B gel mass comprises as percentages by weight, 44.2% gelatin, 7.0% glycerin, 17.0% sorbitol, 6.0% maltitol syrup and 25.2% purified water. The gelatin and gum acacia percentages are adjusted accordingly for 10, 15 and 20% substitution (of the gelatin by gum acacia) of the gelatin.

| Component | 10% Substitution | 15% Substitution | 20% Substitution |
|---|---|---|---|
| Gelatin | 39.8% | 37.6% | 35.4% |
| Gum Acacia | 4.4% | 6.6% | 8.3% |
| Glycerin | 7.0% | 7.0% | 7.0% |
| Sorbitol Solution | 17.6% | 17.6% | 17.6% |
| Maltitol Syrup | 6.0% | 6.0% | 6.0% |
| Purified Water | 25.2% | 25.2% | 25.2% |

TABLE 3

| Sample | Thickness (mils) | Distance at Break (mm) | % Elong. at Break (% $E_b$) | % $E_b$ per mil |
|---|---|---|---|---|
| 3A (Control) | 9.0 | 102.8 | 205.6 | 22.84 |
| 3A (Control) | 10.0 | 112.3 | 224.6 | 22.46 |
| 3A 10% EXTENDER | 10.5 | 142.3 | 284.6 | 27.10 |
| 3A 10% EXTENDER | 10.0 | 142.4 | 284.8 | 28.48 |
| 3A 15% EXTENDER | 10.0 | 126.3 | 252.6 | 25.26 |
| 3A 15% EXTENDER | 10.5 | 134.3 | 268.6 | 25.58 |
| 3A 20% EXTENDER | 12.0 | 138.7 | 274.4 | 23.12 |
| 3A 20% EXTENDER | 12.0 | 130.6 | 261.2 | 21.77 |
| 3B (Control) | 7.5 | 59.46 | 118.92 | 15.86 |
| 3B (Control) | 8.0 | 66.36 | 132.72 | 16.59 |
| 3B 10% EXTENDER | 8.5 | 97.47 | 194.94 | 22.93 |
| 3B 10% EXTENDER | 9.5 | 93.46 | 186.92 | 19.68 |
| 3B 15% EXTENDER | 10.5 | 93.37 | 186.74 | 17.78 |
| 3B 15% EXTENDER | 9 | 89.36 | 178.72 | 19.86 |
| 3B 20% EXTENDER | 9 | 98.30 | 196.60 | 21.84 |
| 3B 20% EXTENDER | 9 | 93.35 | 186.70 | 20.74 |

The control (Control) in all instances shows significantly lower elasticity or the same elasticity (as exemplified by lower elongation to break) as compared to each of the samples where the gum acacia was added. This is surprising in view of the contrary teachings of U.S. Pat. No. 5,614,217 that gum arabic is an elasticity reducing material. The soft gelatin capsule shell materials of the present invention all show increases in elasticity as compared to gelatin-only shell material. It is particularly desirable in the practice of the present invention that the shell material compositions of the present invention exhibit an elongation at break of at least 240%, at least 250%, or even at least 260% with a 10 mil (0.254 mm) dried film (air dried for approximately 5 minutes to a moisture content between about 6–10%).

What is claimed is:

1. A softgel composition comprising:
   a) 30–60% by weight of a film-forming material
   b) 5–35% by weight of a water-dispersible or water-soluble plasticizer
   c) 25–65% by weight purified water wherein the film-forming material comprises gelatin and gum acacia, with gum acacia accounting for 0.5–50% by weight of the total amount of the film-forming material, a dried film having 3–12% by weight of water formed from said composition having no reduced elasticity as compared to a film of same weight of water having the same proportions of the same water-dispersible or water-soluble plasticizer to the total weight of only gelatin film-forming material.

2. A soft gelatin capsule comprising a fill and a shell, wherein the shell comprises a dried composition of claim 1.

3. A process of manufacturing a filled soft gelatin capsule comprising a fill and a shell wherein said fill is provided to an encapsulation area where a sheet of soft gelatin material comprising 30–70% by weight of film-forming material and 58–27% by weight of water-dispersible or water-soluble plasticizer, and the sheet of soft gelatin material encapsulates said fill by the rotary die encapsulation process to form a filled soft gelatin capsule, wherein the shell comprises a dried film having less than about 20% by weight of water formed from said composition, said shell having no reduced elasticity as compared to a shell having the same proportions of the same water-dispersible or water-soluble plasticizer to the total weight of only gelatin film-forming material.

4. The soft gelatin capsule of claim 2, wherein said capsule fill is a liquid, semi-solid, or solid material that has food, nutritional, medical, or cosmetic application.

5. The soft gelatin capsule of claim 2 that has been dried to a shell moisture content of 3–12% by weight.

6. The composition of claim 1 that includes minor additives such as coloring agents, opacifiers, flavors, sweeteners, medicaments, and preservatives.

7. The soft gelatin capsule of claim 2 wherein the shell includes more than 1% but less than 30% by weight of additives selected from the group consisting of coloring agents, opacifiers, flavors, sweeteners, medicaments, and preservatives.

8. The composition of claim 2 wherein said dried film exhibits at least 240% elongation at break with a 10 mil thick dried film.

9. The soft gelatin capsule of claim 2 wherein said shell exhibits at least 240% elongation at break with a 10 mil thick shell.

10. The soft gelatin capsule of claim 4 wherein said shell exhibits at least 240% elongation at break with a 10 mil thick shell.

11. The soft gelatin capsule of claim 2 wherein said shell exhibits at least 250% elongation at break with a 10 mil thick shell.

12. The soft gelatin capsule of claim 8 wherein said water-dispersible or water-soluble plasticizer comprises a non-hygroscopic plasticizer.

13. The soft gelatin capsule of claim 8 wherein said water-dispersible or water-soluble plasticizer comprises a hygroscopic plasticizer.

14. The soft gelatin capsule of claim 9 wherein said water-dispersible or water-soluble plasticizer comprises a non-hygroscopic plasticizer.

15. The softgel capsule of claim 10 wherein said water-dispersible or water-soluble plasticizer comprises a non-hygroscopic plasticizer.

16. The soft gelatin capsule of claim 9 wherein said water-dispersible or water-soluble plasticizer comprises a hygroscopic plasticizer.

* * * * *